(12) United States Patent
Zulyniak

(10) Patent No.: US 9,603,959 B2
(45) Date of Patent: Mar. 28, 2017

(54) METHOD AND APPARATUS FOR STERILIZING ARTICLES

(71) Applicant: Pure Visions Corporation, Kamloops (CA)

(72) Inventor: Pamela Dawn Zulyniak, Kamloops (CA)

(*) Notice: Subject to any disclaimer, the term of this patent is extended or adjusted under 35 U.S.C. 154(b) by 106 days.

(21) Appl. No.: 14/745,265

(22) Filed: Jun. 19, 2015

(65) Prior Publication Data

US 2016/0367711 A1    Dec. 22, 2016

(51) Int. Cl.
*A61L 2/10* (2006.01)
*H01H 35/00* (2006.01)

(52) U.S. Cl.
CPC .............. *A61L 2/10* (2013.01); *H01H 35/00* (2013.01)

(58) Field of Classification Search
USPC ................................................ 250/455.11
See application file for complete search history.

(56) References Cited

U.S. PATENT DOCUMENTS

2010/0028201 A1* 2/2010 Neister ................. A61L 2/0011
                                                                422/24
2010/0193709 A1* 8/2010 Dalton ...................... A61L 2/10
                                                                250/504 R

* cited by examiner

*Primary Examiner* — Kiet T Nguyen
(74) *Attorney, Agent, or Firm* — Richard D. Okimaw

(57) ABSTRACT

An apparatus for sterilizing articles comprises a body extending between first and second ends having a bottom surface and defining an interior cavity into the bottom surface thereof and an ultraviolet light source located in the interior cavity. The apparatus further includes a power source operably connected to the ultraviolet light source and at least one proximity sensor disposed along the bottom surface adapted to sense proximity of the bottom surface to an object, wherein the at least one proximity sensor is adapted to permit ultraviolet light source to be illuminated only when the bottom surface is proximate to the object.

16 Claims, 5 Drawing Sheets

METHOD AND APPARATUS FOR STERILIZING ARTICLES

BACKGROUND OF THE INVENTION

1. Field of Invention

The present invention relates to sterilizing articles in general and in particular to a method and apparatus for sterilizing exercise mats.

2. Description of Related Art

In the field of exercise equipment, one article which frequently needs to be sterilized are the mats of on which the exercise is to be completed. In particular, yoga mats are known to accumulate sweat and/or dirt during the course of exercise thereon providing a location for the grown of bacteria or other organisms which may be undesirable or hazardous. It is therefore required to clean and remove such bacteria and other organisms.

Conventional methods of removing bacteria and other organisms from exercise mats have not been satisfactory. In particular, some methods may leave a residue or odor on the exercise mat where chemicals are used while other methods may be insufficient to completely sterilize the surface. The use of chemicals or solutions may also be undesirable in some fields such as yoga or the like.

Attempts have also been made to provide a method of disinfecting exercise mats with an ultraviolet light source which may be waived over an object to kill any bacteria thereon thereby sterilizing it. One disadvantage of the use of ultraviolet light is that the ultraviolet light may also be harmful to people operating the light source. In particular, ultraviolet light is known to be harmful to a users eyes, and therefore care must be taken to ensure that the ultraviolet light is not directed towards the user's eyes. Measures to ensure that such ultraviolet light may not be directed towards a users eyes has been to provide the light source with a downwardly oriented light and an orientation or position sensor it to shut off the lights when the light source is be aimed in an upward direction. Such solutions have disadvantageously not adequately prevented the light source from being aimed at a user as the light source may still be positioned above the user in a downwardly oriented position wherein it would still remain on potentially damaging a person's eyes. Additionally, such orientation or position switches limit the flexibility of such a device as it may not be utilized to sterilize vertical services. A further disadvantage of such designs is that it may be difficult for a user to know and maintain the proper distance from the object to ensure proper sterilization.

SUMMARY OF THE INVENTION

According to a first embodiment of the present invention there is disclosed an apparatus for sterilizing articles comprising a body extending between first and second ends having a bottom surface and defining an interior cavity into the bottom surface thereof and an ultraviolet light source located in the interior cavity. The apparatus further includes a power source operably connected to the ultraviolet light source and at least one proximity sensor disposed along the bottom surface adapted to sense proximity of the bottom surface to an object, wherein the at least one proximity sensor is adapted to permit ultraviolet light source to be illuminated only when the bottom surface is proximate to the object.

The at least one proximity sensor may comprise two proximity sensors located proximate to the first and second ends of the body. The at least one proximity sensor may be adapted to sense contact with the object. The at least one proximity sensor may comprise a pressure switch.

The pressure switch may include a low friction body adapted to engage the object so as to transmit the pressure between body and the object to the pressure switch. The low friction body may comprise a sliding surface. The low friction body may comprise a roller.

The body may include a socket located proximate to each of the first and second ends of the body having the pressure switch and roller located therein. The roller may be rotatably supported upon a carriage slidably located within the socket. The pressure switch may sense upward movement of the carriage within the socket.

The power source may be operably connected to the ultraviolet light source through a control circuit. The control circuit may include a power switch adapted to turn on the ultraviolet light source when the at least one proximity switch determines that the bottom is proximate to the object. The control circuit may include a timer adapted to begin timing after the power switch is activated, wherein the timer is further adapted to switch the light from a standby state in which the ultraviolet light source may be illuminated if the proximity sensors determine the bottom surface of the body is proximate to said object to an off state when a predetermined time expires.

The apparatus may further comprise a protective cage located around the ultraviolet light source. The apparatus may further comprise a handle extending from the body. The handle may be pivotally connected to the body.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention wherein similar characters of reference denote corresponding parts in each view.

DETAILED DESCRIPTION

Figure 1:
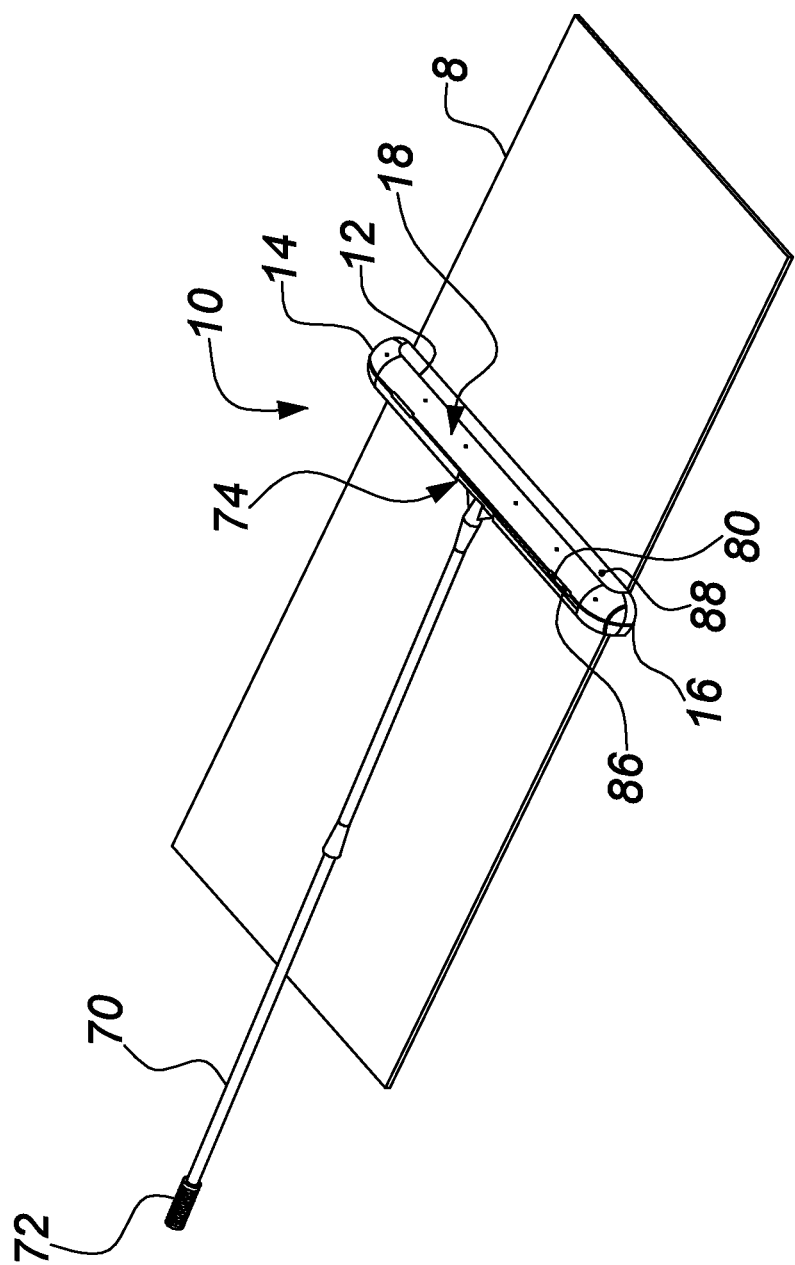
FIG. 1 is a perspective view of an apparatus for sterilizing an exercise mat according to a first embodiment of the present invention applied over an exercise mat.
Figure 2:
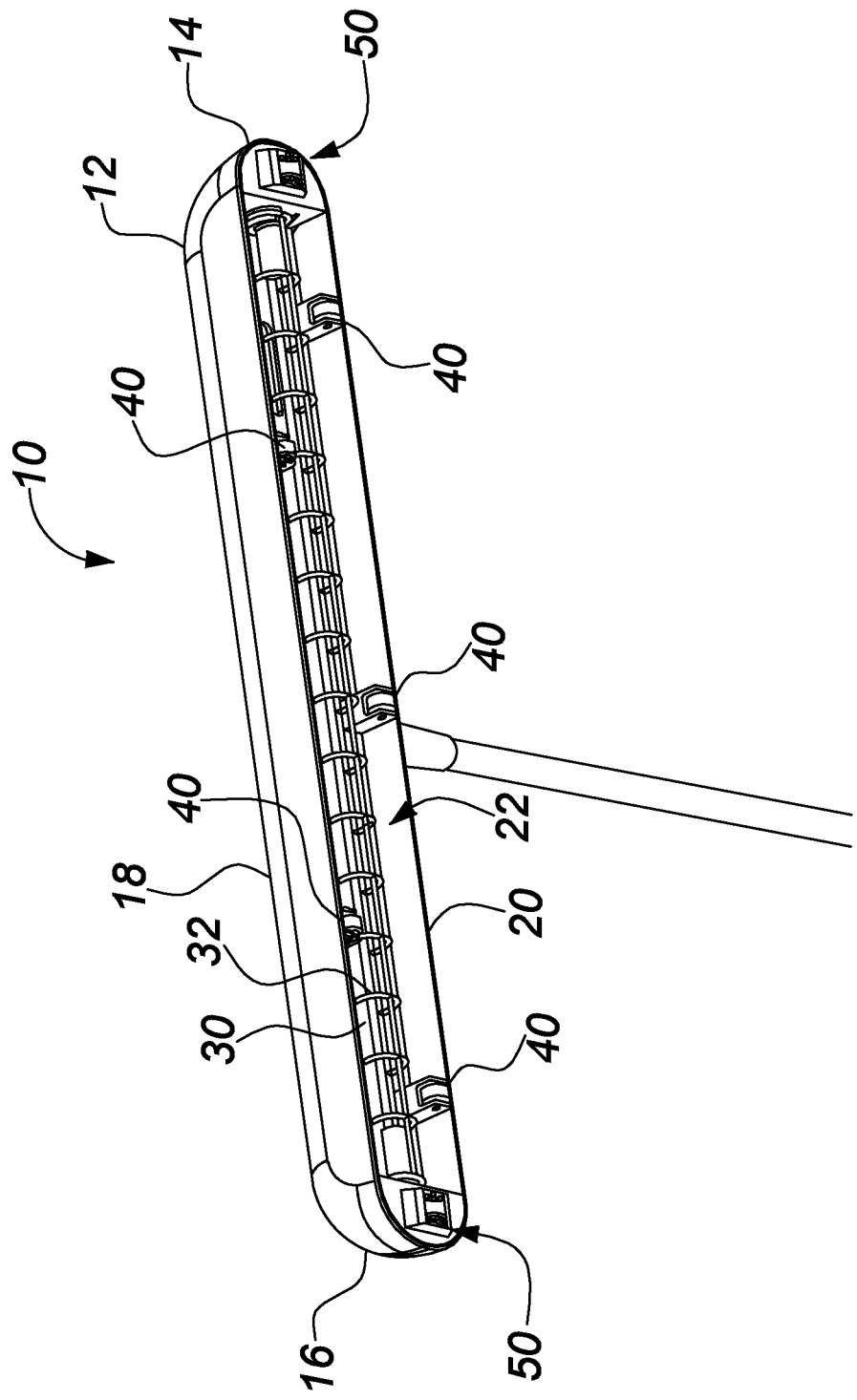
FIG. 2 is a bottom perspective view of the apparatus of FIG. 1.

Referring to FIGS. 1 and 2, an apparatus for sterilizing articles according to a first embodiment of the invention is shown generally at 10. As illustrated in FIG. 1, the apparatus 10 may be utilized to sterilize exercise mats such as, yoga mats by way of non-limiting example, although it will also be appreciated that the apparatus may also be utilized to sterilize other articles and surfaces as well. The apparatus 10 comprises a body 12 having an ultraviolet light source 30 (not shown in FIG. 1) such as ultraviolet light C (UVC) located therein. As described greater detail below, the apparatus 10 includes a power source 82 (shown in FIG. 5) and at least one proximity sensor 60 adapted to determine if bottom of the body and therefore the ultraviolet light source 30 is proximate to a surface to be sterilized before illuminating the ultraviolet light source.

As illustrated in FIGS. 1 and 2, the body 12 comprises an elongate body extending between first and second ends, 14 and 16, respectively. As illustrated, the body 12 may have a substantially cylindrical top surface 18 although it will be appreciated that other shapes may be useful as well. As illustrated in FIG. 2, the body 12 has a substantially planar bottom surface 20 having a cavity 22 formed therein. An ultraviolet light source 30 is located within the cavity 22 so as to be surrounded by sidewalls of the body thereby enclosing the ultraviolet light source 30 and preventing ultraviolet light from being radiated in directions other than past the bottom surface 20. The ultraviolet light source 30 may comprise any known ultraviolet light bulbs, such as by way of non-limiting example, tube lightbulbs, globe light bulbs and LED light bulbs. As illustrated in FIG. 2, a cage 32 may be located around the ultraviolet light source 30 to protect it from impacts and the like.

The bottom surface 20 of the body 12 is provided with at least one low friction body for engagement of the body 12 upon the surface to be sterilized. By way of non-limiting example, the low friction bodies may comprise a plurality of rollers 40 disposed along the bottom surface 20. Optionally, sliders or felt pads may also be utilized. As illustrated in FIG. 2, the body 12 may include a plurality of rollers to each side of the cavity 22 so as to support the body away from a surface by a predetermined distance. The distance from the bottom surface 20 to the surface to be sterilized may be selected to permit adequate containment of the ultraviolet light while preventing the edges of the body 12 from catching on irregularities in the mat 8 or other article such as by way of non-limiting example, between ¼ and 1 inch (6 and 25 mm). Similarly, the ultraviolet light source will be located above the surface of the article to be sterilized by a distance selected based upon the power level and number of the selected ultraviolet light source so as to provide adequate ultraviolet light to the surface to be sterilized. By way of non-limiting example, it has been found that a distance of between ½ and 2 inches has been useful for a single 8 W bulb although it will be appreciated that other distances will be suitable for different bulb types and quantities.

Figure 3:
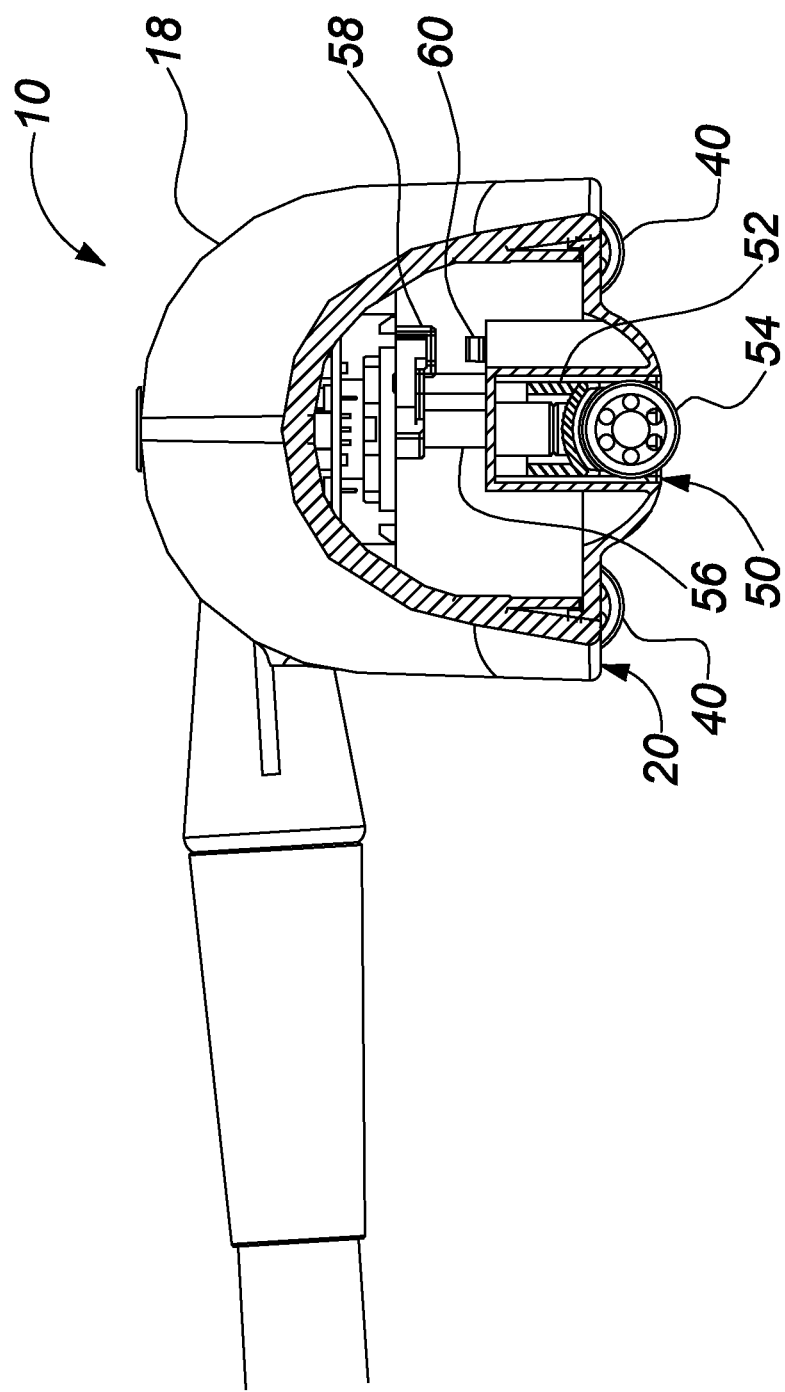
FIG. 3 is a cross sectional view as taken along the line 3-3 of the apparatus of FIG. 2.
Figure 4:
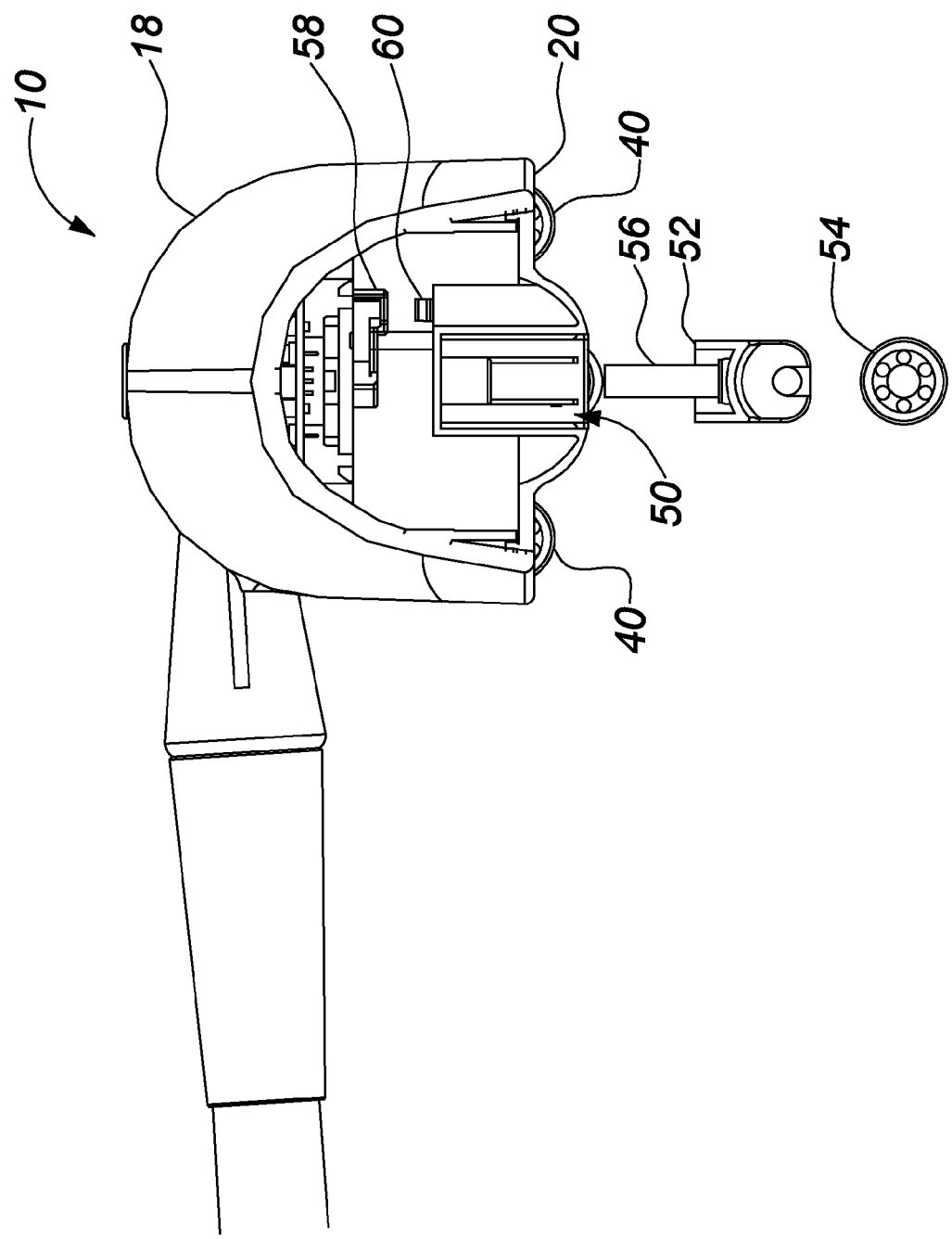
FIG. 4 is an exploded cross sectional view as taken along the line 3-3 of the apparatus of FIG. 2.

As illustrated in FIG. 2, the body 12 may include rollers 54 supported within sockets 50 proximate to the first and second ends 14 and 16 of the body. Turning now to FIGS. 3 and 4, the sockets 50 are formed into the bottom surface 20 of the body. Each socket 50 is adapted to slidably receive a chassis 52 therein wherein each chassis rotatably supports a roller 54 at a bottom end thereof. Each socket 50 as a switch or sensor therein adapted to sense when the roller 54 has been engaged upon a surface and displaced inwardly within the socket so as to determine that the bottom surface 20 is bearing against an object. In particular, as illustrated in FIGS. 3 and 4, each chassis 52 may include a shaft 56 extending upwardly therefrom to a head 58 located above the socket 50. The head 58 extends past the edges of the socket 50 to engage upon a proximity sensor 60 at a downward position corresponding to when the chassis is extended to a bottom most position corresponding to when the bottom surface 20 is not bearing against an object. In such embodiments, the sensor 60 may comprise a normally closed switch. Optionally, the sensor 60 may be located above the head 58 to indicate to the control circuit when the chassis 52 has been compressed into the socket in which case the switch may comprise a normally open switch. It will be appreciated that the chassis 52 will be biased within the socket 50 to a bottom most position by springs or the like. It will also be appreciated that other methods of determining when the bottom surface 20 is bearing against a surface may also be utilized such as by way of non-limiting example inductive, ultrasonic, photocell or other proximity sensors.

As illustrated in FIG. 1, the apparatus 10 may include a power button 80 adapted to turn on the ultraviolet light source 30, a standby light 86 adapted to be illuminated when the apparatus is properly positioned proximate to the mat and a charging port 88 adapted to receive a power cord (not shown) for charging the battery of the apparatus.

Figure 5:
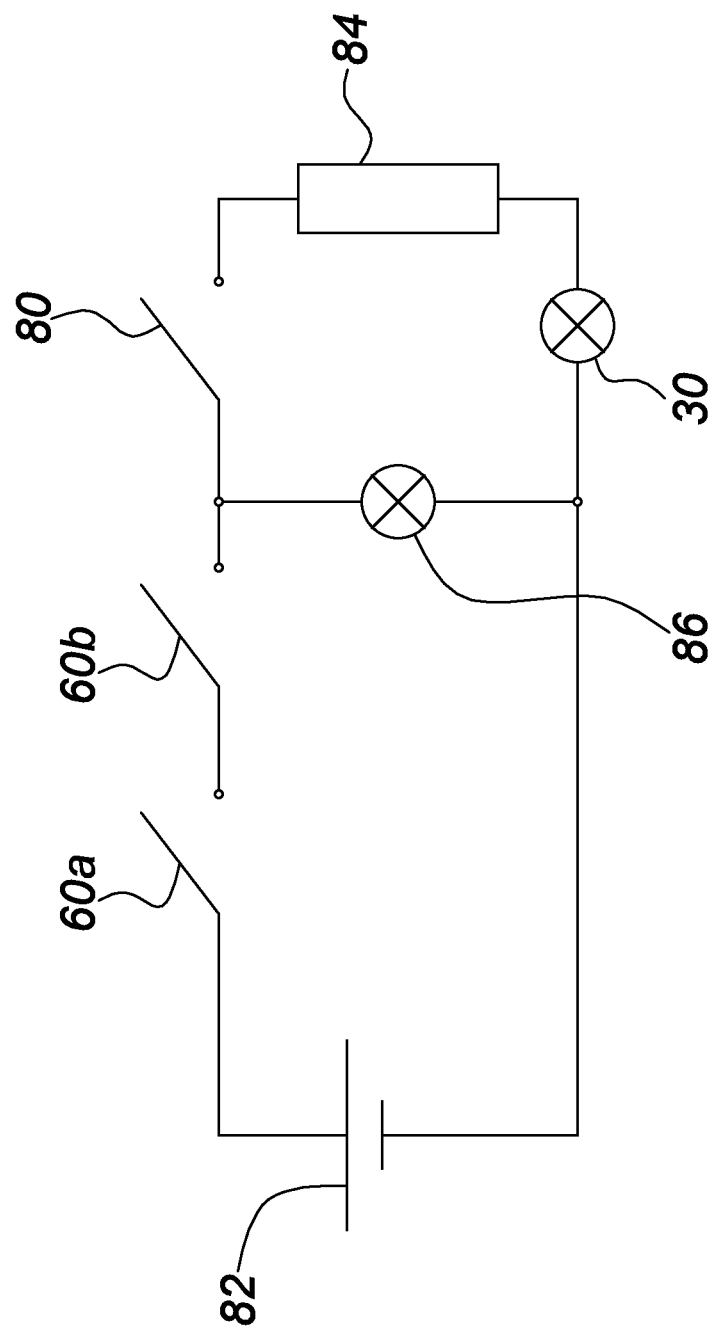
FIG. 5 is a wiring diagram for the control circuit of the apparatus of FIG. 1 according to a first embodiment of the present invention.

Turning now to FIG. 5, an illustrative wiring diagram of one embodiment of a control circuit for operating the apparatus is illustrated. The apparatus 10 may include a power source 82 one or more proximity switches 60*a* and 60*b* as set out above, the ultraviolet light source 30 and a timer 84. As illustrated, after the power button 80 has been depressed, the ultraviolet light source 30 is only permitted to be illuminated when both of the proximity switches 60*a* and 60*b* have been closed signalling that both ends of the apparatus are bearing against a surface. Thereafter the timer 84 will measure a predetermined length of time before inactivating the apparatus and returning it from a ready state in which the ultraviolet light source could be illuminated to one in which the ultraviolet light source could not be illuminated until the user depresses the power button again and restarts the time. By way of non-limiting example the timer could have a time limit set to preserve battery power while allowing a user sufficient time to sterilize a number of exercise mats. Optionally, the apparatus may also include a standby light 86 which is illuminated after the proximity switches have been closed so as to indicate to a user that the apparatus is in the correct position.

It will also be appreciated that although a simple circuit is illustrated in FIG. 5 and described herein, other methods of controlling the ultraviolet light source may also be used, such as by way of non-limiting example, a microprocessor, or other electronic control circuitry. More generally, in this specification, including the claims, the term "control circuit" is intended to broadly encompass any type of device or combination of devices capable of performing the functions described herein, including (without limitation) other types of microprocessors, microcontrollers, other integrated circuits, other types of circuits or combinations of circuits, logic gates or gate arrays, or programmable devices of any sort, for example, either alone or in combination with other such devices located at the same location or remotely from each other, for example. Additional types of control circuits will be apparent to those ordinarily skilled in the art upon review of this specification, and substitution of any such other types of processor circuits is considered not to depart from the scope of the present invention as defined by the claims appended hereto.

As illustrated in FIGS. 1 and 2, the body 12 may optionally include a handle 70 for operation by a user. The handle 70 may include a hand grip 72 at a distal end thereof and may be pivotally connected to the body 12 at a pivot connection 74 as are commonly known. Optionally, the handle 70 may include the power button 80 as set out above for ease of operation.

While specific embodiments of the invention have been described and illustrated, such embodiments should be considered illustrative of the invention only and not as limiting the invention as construed in accordance with the accompanying claims.

What is claimed is:

1. An apparatus for sterilizing articles comprising:
a body extending between first and second ends having a bottom surface and defining an interior cavity into said bottom surface thereof;
an ultraviolet light source located in said interior cavity;
a power source operably connected to said ultraviolet light source;
at least one proximity sensor disposed along said bottom surface adapted to sense proximity of said bottom surface to an object, wherein said at least one proximity sensor is adapted to permit ultraviolet light source to be illuminated only when said bottom surface is proximate to said object.

2. The apparatus of claim 1 wherein said at least one proximity sensor comprises two proximity sensors, wherein each proximity sensor is located proximate to one of said first and second ends of said body.

3. The apparatus of claim 1 wherein said at least one proximity sensor is adapted to sense contact with said object.

4. The apparatus of claim 3 wherein said at least one proximity sensor comprises a pressure switch.

5. The apparatus of claim 4 wherein said pressure switch includes a low friction body on a distal end thereof adapted to engage said object so as to transmit said pressure between body and said object to said pressure switch.

6. The apparatus of claim 5 wherein said low friction body includes a sliding surface disposed along a bottom thereof.

7. The apparatus of claim 5 wherein said low friction body comprises a roller.

8. The apparatus of claim 7 wherein said body includes a socket located proximate to each of said first and second ends of said body having said pressure switch and roller located therein.

9. The apparatus of claim 8 wherein said roller is rotatably supported upon a carriage slidably located within said socket.

10. The apparatus of claim 9 wherein said pressure switch senses upward movement of said carriage within said socket.

11. The apparatus of claim 1 wherein said power source is operably connected to said ultraviolet light source through a control circuit.

12. The apparatus of claim 11 wherein said control circuit includes a power switch adapted to turn on said ultraviolet light source when said at least one proximity sensor determines that said bottom is proximate to said object.

13. The apparatus of claim 12 wherein said control circuit has a timer adapted to begin timing after said power switch is activated, wherein said timer is further adapted to switch said light from a standby state in which said ultraviolet light source may be illuminated if said proximity sensors determine said bottom surface of said body is proximate to said object to an off state when a predetermined time expires.

14. The apparatus of claim 1 further comprising a protective cage located around said ultraviolet light source.

15. The apparatus of claim 1 further comprising a handle extending from said body.

16. The apparatus of claim 15 wherein said handle is pivotally connected to said body.

* * * * *